US010436760B2

(12) United States Patent
Van Loon et al.

(10) Patent No.: US 10,436,760 B2
(45) Date of Patent: Oct. 8, 2019

(54) HUMIDITY INDICATING COMPOSITION

(71) Applicant: BELISARIUS B.V., Capelle aan den Ijssel (NL)

(72) Inventors: Sander Van Loon, Capelle aan den Ijssel (NL); Alejandro Gutierrez, Capelle aan den Ijssel (NL); Gwenola Le Mouée, Capelle aan den Ijssel (NL); Marco Verschuur, Capelle aan den Ijssel (NL)

(73) Assignee: BELISARIUS B.V., Capelle aan den Ijssel (NL)

( * ) Notice: Subject to any disclaimer, the term of this patent is extended or adjusted under 35 U.S.C. 154(b) by 124 days.

(21) Appl. No.: 15/367,532

(22) Filed: Dec. 2, 2016

(65) Prior Publication Data
US 2017/0160247 A1 Jun. 8, 2017

(30) Foreign Application Priority Data
Dec. 2, 2015 (EP) ..................................... 15197635

(51) Int. Cl.
*G01N 31/22* (2006.01)
*B01J 20/26* (2006.01)
*B01J 20/22* (2006.01)
*B01J 20/08* (2006.01)
*B01J 20/10* (2006.01)
*B01J 20/04* (2006.01)
*B01J 20/32* (2006.01)

(52) U.S. Cl.
CPC .......... *G01N 31/222* (2013.01); *B01J 20/043* (2013.01); *B01J 20/08* (2013.01); *B01J 20/103* (2013.01); *B01J 20/22* (2013.01); *B01J 20/262* (2013.01); *B01J 20/3212* (2013.01); *B01J 20/3293* (2013.01); *G01N 31/221* (2013.01)

(58) Field of Classification Search
CPC .... G01N 31/222; G01N 31/221; G01N 21/81; B01J 20/3293; B01J 20/3212; B01J 20/262; B01J 20/103; B01J 20/08; B01J 20/22; B01J 20/043; B01J 20/24; B01J 20/10; B01J 20/16; B01J 20/28026; B01J 20/12; B01J 20/261; B01J 20/14; B01J 20/18; B01J 20/3007; B01J 20/046; B01J 20/3441; B01J 2220/46; B01J 20/28047; B01J 20/02; B01J 20/2805; C08G 18/4825; C08G 18/778; C08G 18/755; C08G 18/718; C08G 18/0885; C08G 18/3821; C08G 18/289; C08G 18/283; C08G 2190/00; B01D 53/28; B01D 2253/106; B01D 2253/112; B01D 2253/202; B01D 2259/40094; B01D 2253/108; B01D 2253/11; B01D 53/261; B01D 53/0407; B01D 2252/202; B01D 2257/90; B01D 2253/20; B01D 2252/50; B01D 2257/104; B01D 2252/103; B01D 53/263; B65D 79/02; B65D 81/268; B65D 65/42; B65D 81/266; G06K 19/0717; G06Q 30/0185; G08B 13/2448; G08B 13/2451

See application file for complete search history.

(56) References Cited

U.S. PATENT DOCUMENTS

| | | | |
|---|---|---|---|
| 3,904,373 A | 9/1975 | Harper | |
| 5,266,486 A | 11/1993 | Fraatz et al. | |
| 7,316,198 B2 * | 1/2008 | Yamakawa | G01N 21/81 |
| | | | 116/206 |
| 7,743,642 B2 * | 6/2010 | Chiba | B01D 53/261 |
| | | | 73/29.04 |
| 2003/0215644 A1 * | 11/2003 | Deshpande | B05D 1/08 |
| | | | 428/416 |
| 2003/0232942 A1 * | 12/2003 | Roesler | C08G 18/0885 |
| | | | 528/10 |
| 2004/0051081 A1 * | 3/2004 | Moreton | G01N 31/222 |
| | | | 252/408.1 |
| 2005/0106735 A1 * | 5/2005 | Song | G01N 21/81 |
| | | | 436/39 |
| 2006/0188688 A1 * | 8/2006 | Sasaki | B01D 53/02 |
| | | | 428/68 |
| 2012/0329169 A1 * | 12/2012 | Knyrim | G01N 31/222 |
| | | | 436/163 |
| 2014/0121313 A1 * | 5/2014 | Hu | C08K 3/26 |
| | | | 524/425 |

FOREIGN PATENT DOCUMENTS

| | | |
|---|---|---|
| EP | 2 085 132 A1 | 8/2009 |
| EP | 2 339 340 A1 | 6/2011 |
| GB | 2 420 849 A | 6/2008 |
| WO | 9410553 A1 | 5/1994 |

OTHER PUBLICATIONS

K.T.V. Grattan et al., "Use of sol-gel techniques for fibre-opic sensor applications", Sensors and Actuators, vol. 26, No. 1-3, Mar. 1, 1991, pp. 483-487.

G.E. Badini et al., "Impregnation of a pH-sensitive dye into sol-gels for fibre chemical sensors", Analyst, vol. 120, No. 4, Apr. 1995, pp. 1025-1028.

Delana A. Nivens et al., Multilayer sol-gel membranes for optical sensing applications: single layer pH and dual layer CO2 and NH3 sensors, Talanta, vol. 58, Jul. 1, 2002, pp. 543-550.

Delana A. Nivens et al., "A fiber-optic pH sensor prepared using a base-catalyzed organo-silica sol-gel", Analytica Chimica Acta, vol. 376, No. 2, Dec. 11, 1998, pp. 235-245.

* cited by examiner

*Primary Examiner* — Lore R Jarrett
(74) *Attorney, Agent, or Firm* — Hudak, Shunk & Farine Co. LPA

(57) ABSTRACT

The invention relates to a humidity indicating composition comprising (a) an organic pH indicator dye compound, (b) a Bronsted base comprising an organosilane, (c) a moisture-curable binder, (d) an optional rheology additive and (e) an optional alkaline filler.

18 Claims, No Drawings

HUMIDITY INDICATING COMPOSITION

FIELD OF THE INVENTION

The present invention relates to a humidity indicating composition, to a humidity indicating article comprising said humidity indicating composition and to a process for preparing said humidity indicating article.

BACKGROUND OF THE INVENTION

When using materials which are susceptible to moisture, it is desirable to know whether those materials have been exposed or are being exposed to a particular level of humidity of the surrounding atmosphere. Humidity indicators are commonly applied to materials and objects to indicate the relative humidity levels in the surrounding air. In desiccants or desiccant containing articles, humidity indicators are known to be applied to the desiccant itself or to the container to indicate the saturation level of the desiccant. Known desiccant containers are made from non-woven fabrics, metal, paper and plastics. When the level of moisture absorbed by the desiccant in the container reaches a specific level of saturation, the desiccant in the container has to be replaced or regenerated. Known containers have a patterned design which changes color depending on the moisture level in order for the user to determine whether the maximum limit has been reached.

Known desiccants and desiccant containers have humidity indicating compositions based on cobalt dichloride or other metal salts. However, these compositions contain considerable amounts of heavy metals and halide anions, which are undesirable in view of the environmental considerations.

For example, EP2085132 discloses a regenerative dehumidifying bag comprising a water vapour-permeable pouch (1), a desiccant material (2) filled in the pouch (1) and a colour-changeable humidity indicator (3) printed on an outer surface of the pouch (1). The humidity indicator (3) includes a base figure (31) of blue colour printed on an outer surface of the pouch (1) and a colour-changeable marking (32) formed as a mark disposed within the base figure (31) of the humidity indicator (3). The colour-changeable marking (32) includes a colour-changeable ink comprising cobalt chloride. Upon saturation of moisture absorbed by the desiccant material (2) in the pouch (1), the marking (32) with the cobalt chloride changes colour from a blue colour to a pink colour so as to be distinguishable from the blue colour of the base figure (31), indicating that the desiccant material (2) should be replaced.

EP2339340 discloses a humidity indicating composition containing no halogen compounds and no heavy metals. In particular, EP2339340 discloses a humidity indicating composition comprising (a) an organic pH indicator dye compound, (b) a Bronsted acid or base, (c) a polyol having the general formula HOCH—($CH_2$)n-CHOH, wherein n can be 0, 1, 2, 3 or 4, and (d) a solvent; wherein said components (a), (b), (c) and (d) do not contain halogen and/or heavy metals. The composition is used for preparing a humidity indicator card by applying the composition onto a sheet substrate and allowing the solvent (d) to evaporate. The evaporation of the solvent requires an extra step.

Other problems of existing indicator compositions are that they degrade and lose their indicating function over time due to exposure to condensation and steam during the regeneration process. This washes out the dye compounds and reduces product life.

There is a need in the industry for a humidity indicating composition which can be used for making various types of humidity indicating article.

SUMMARY OF THE INVENTION

It is an object of the present invention to provide a humidity indicating composition in which the above-described and/or other problems are solved.

Accordingly, the present invention provides a humidity indicating composition comprising
(a) an organic pH indicator dye compound,
(b) a Bronsted base comprising an organosilane,
(c) a moisture-curable binder,
(d) an optional rheology additive and
(e) an optional alkaline filler.

DETAILED DESCRIPTION OF THE INVENTION

The composition according to the invention provides a good sensing function.

When the composition according to the invention is applied to the substrate, (b) the organosilane and (c) the moisture-curable binder cure with moisture from the air and forms a coating. The cured organosilane and binder form a network which binds the components of the composition to the substrate. This prevents the loss of (a) the organic pH indicator dye compound from the coating when the coating is exposed to severe conditions, for example during the regeneration process in which the coating is exposed to steam and condensed water at high temperatures. Accordingly, the coating according to the invention can retain its function during the regeneration process. Therefore, in preferred embodiments, the article according to the invention comprising the coating according to the invention is a reusable article.

Preferably, the composition according to the invention contains little or no solvent such as water, methanol, ethanol or acetone. Preferably, the total amount of water, methanol, ethanol and acetone is less than 0.01 parts by weight, more preferably less than 0.001 parts by weight, relative to 1 part by weight of the total humidity indicating composition. This is advantageous in that the composition does not require evaporation of the solvent, which allows the formation of the coating to be fast. It will be appreciated that any methanol or ethanol formed after the reaction of the components of the composition with water, such as the reaction of components (b) and/or (c) with water, is not considered as elements of the composition according to the invention.

Preferably, the composition according to the invention does not contain an element of group 17 of the periodic system of elements which comprises F, Cl, Br, I and At.

Preferably, the composition according to the invention does not contain atoms or ions of a heavy metal. Heavy metal is herein understood to mean cobalt, copper, zinc.

Preferably, the total weight of the components (a)-(e) is at least 90 wt %, at least 95 wt %, at least 98 wt %, at least 99 wt % or 100 wt % of the total composition.

(a) Organic pH Indicator Dye Compound

The organic pH indicator dye compound is well-known. Suitable examples include the ones described in EP2339340, which is reproduced here as follows.

The organic pH indicator dye compound is an organic compound absorbing light from the spectrum visible to a human's eye such that the compound appears colored. The specific wavelength or range of wavelengths of the visible spectrum absorbed by the compound changes in reaction to a change in pH such the color impression caused by the compound changes. The compound is thus suitable to visually indicate a change in pH. The specific pH range at which the color transition takes place depends on the molecular structure of the compound.

Commonly known organic pH indicator dye compounds are litmus, cyanidine, xylenol blue, Neutral red, Thymol blue, Phenolphthalein, Alizarin, Alkaline blue, Thymolphthalein each of which is suitable for being employed as component (a) in the humidity indicating composition according to the present invention.

Examples of preferred organic pH indicator dye compounds include a compound having a triphenylmethan substructure or a phenazin substructure.

A triphenylmethan substructure is present in xylenol blue, Thymol blue, Phenolphthalein, Alizarin, Alkaline blue, Thymolphthalein.

A phenazin substructure is present in Neutral red.

Further preferred organic pH indicator dye compounds include alizarin red S, alizarin yellow GG, alizarin yellow R, brilliant yellow, bromocresol green, bromophenol blue, bromothymol blue, chlorophenol red, clayton yellow, congo red, cresol red, crystal violet, dimethyl yellow, erythrosine, malachite green, metacresol purple, metanil yellow, methyl green, methyl orange, methyl red, neutral red, phenolphthalein, phenol red, paramethyl red, quinaldine red, resazurin, thymolphthalein and thymol blue.

As mentioned above, the specific pH range at which the color transition takes place depends on the molecular structure of the compound.

The following organic pH indicator dye compound undergoes a color transition at a pH range of 10-12:
clayton yellow, alizarin yellow GG, alizarin yellow R, thymolphthalein The following organic pH indicator dye compound undergoes a color transition at a pH range of 7-9.5:
phenolphthalein, thymol blue, metacresol purple, cresol red, phenol red, brilliant yellow, neutral red The following organic pH indicator dye compound undergoes a color transition at a pH range of 5-6.5:
bromothymol blue, methyl red, resazurin The following organic pH indicator dye compound undergoes a color transition at a pH range of 1-4.5:
chlorophenol red, alizarin red S, bromocresol green, methyl orange, congo red, dimethyl yellow, bromophenol blue, erythrosine, metanil yellow, paramethyl red, quinaldine red, crystal violet, malachite green, methyl green Preferably, the organic pH indicator dye compound undergoes a color transition at a pH range which lies within a pH range of 5-12, preferably 7-12, for example 7-9.5.

(b) Bronsted Base

The Bronsted base is well-known and the description in EP2339340 also applies here, which is reproduced here as follows.

A Bronsted base is a compound that can receive a proton. The Bronsted base component of the humidity indicating composition according to the present invention thus is capable of receiving a proton from the organic pH indicator dye compound (a) present in the composition in a dynamic equilibrium. Under the influence of the relative humidity of the surrounding atmosphere, the equilibrium is shifted more to the side of the protonated organic pH indicator dye compound (a) or more to the side of the unprotonated organic pH indicator dye compound (a) which results in a change of color of the organic pH indicator dye compound (a).

The pH generated by the Bronsted acid or base is influenced by the amount of said Bronsted acid or base and by its dissociation constant. Therefore, by varying the amount of Bronsted acid or base relative to the amount of a specific organic pH indicator dye compound (a), the specific relative humidity at which the color transition of the organic pH indicator dye compound (a) takes place can be influenced.

Alternatively or additionally, the pH generated can be influenced by selecting a specific Bronsted acid or base having a different dissociation constant. Thus, the relative humidity at which the color transition of a specific organic pH indicator dye compound (a) takes place can be also influenced by varying the specific Bronsted base.

Preferably, the Bronsted acid or base is present in the humidity indicating composition in an amount of 1 to 5000 parts by weight, more preferably 1000 to 3000 parts by weight, more preferably 1500 to 2500 parts by weight, relative to 1 part by weight of said organic pH indicator dye compound.

The Bronsted base is or comprises an organosilane. Preferably, the organosilane comprises a Bronsted base group selected from the group consisting of NH2, NHR, NR2, amide and pyridine functionalities, wherein R is a C1-C20 alkyl substituent or a C6-C20 aryl substituent.

Preferably, the organosilane is aminoalkyltrialkoxysilane, for example
3-aminomethyltrimethoxysilane,
3-aminomethyltriethoxysilane,
3-aminomethyltripropoxysilane,
3-aminoethyltrimethoxysilane,
3-aminoethyltriethoxysilane,
3-aminoethyltripropoxysilane,
3-aminopropyltrimethoxysilane,
3-aminopropyltriethoxysilane,
3-aminopropyltripropoxysilane.

An example of the Bronsted base comprising an organosilane is 3-aminopropyltriethoxysilane, commercially available as Dynasylan AMEO from Evonik Industries.

(c) Moisture-Curable Binder

The moisture-curable binder is preferably selected from the group consisting of silicone-based binders, acrylate-based binders and polyurethane-based binders.

Preferably, the moisture-curable binder is a silicone-based binder. When the composition according to the invention is applied to the substrate, the organosilane (b) and the silicone-based binder (c) cure with moisture (in the air) and form a siloxane network of the coating while binding to the substrate. The siloxane network gives high hydrophobicity to the coating. Therefore, the coating according to the invention is water resistant and leaching out of the coating ingredients is prevented.

Suitable examples of the silicone-based binders are polyether-based silane-terminated polymers. An example of the polyether-based silane-terminated polymer is commercially available as Geniosil XB502 from Wacker Chemie AG.

(d) Rheology Additive

Preferably, the composition according to the invention comprises a rheology additive.

The rheology additive controls the rheological properties of the composition to facilitate the application of the composition onto a substrate. Suitable choice of the type and the amount of the rheology additive prevents the composition according to the invention to further leach along the substrate.

Suitable types and amounts of the rheology additives may be easily selected by the skilled person to obtain desired rheological properties depending on the substrate to which the composition according to the invention is applied.

Suitable examples of the rheology additive include polyhydroxycarboxylic acid esters.

An example of the polyhydroxycarboxylic acid ester is commercially available as Byk R606 from BYK Additives & Instruments.

Other types of suitable examples of the rheology additive include particles of fumed silica and particles of fumed silica and aluminium oxide. An example of particles of fumed silica is commercially available as Aerosil 200 from Evonik Industries. An example of particles of fumed silica and aluminium oxide is commercially available as Aerosil COK84 from Evonik Industries.

Preferably, the weight ratio of the polyhydroxycarboxylic acid esters on one hand and the particles of fumed silica the particles of fumed silica and aluminium oxide on the other hand is 1:5-5:1, more preferably 1:3-3:1 or 1.3:1-1:1.3.

(e) Alkaline Filler

It is desirable that a clear color transition of the composition occurs as a result of the change in the relative moisture. Accordingly, it is desirable that the composition will have a pH for exhibiting a first color at a dry state and another pH for exhibiting another color distinct from the first color at a wet state.

The composition according to the invention may comprise an alkaline filler. The alkaline filler may be used to adjust the pH of the composition to ensure that a distinct change of the color occurs between the dry state and the wet state.

For example, thymol blue has a red color at pH of less than around 2.5, yellow at pH of around 2.5-8, green at pH of 8-9, blue at pH of more than 9. It is desirable if the composition has pH of less than 8 at a completely dry state and pH of more than 9 at a completely wet state, as it would achieve a clear indication of the moisture level. In this case, the composition will change color from yellow (dry) to green (partly wet) to blue (completely wet) depending on the moisture level, clearly indicating the moisture level. It is less desirable if a composition has pH of less than 8 at a completely dry state and pH of 8-9 at a completely wet state. In this case, it is difficult to distinguish between the partly wet state (green) and the completely wet state (green). Accordingly, the composition according to the invention may comprise an alkaline filler in order to adjust the pH of the composition in the wet state. As the composition absorbs more water, the alkaline filler shifts the pH of the composition to a higher value.

Preferably, the alkaline filler is a carbonate of an alkaline earth metal, e.g. a carbonate of magnesium and/or calcium. Preferably, the carbonate is partially hydrated.

An example of partially hydrated magnesium-calcium carbonate is commercially available as Portafill H 5.

Preferably, the composition according to the invention comprises (e) the alkaline filler and (a) the organic pH indicator dye compound undergoes a color transition at a pH range which lies within a pH range of 5-12, preferably 7-12, for example 7-9.5.

Most preferably, the composition according to the invention comprises partially hydrated magnesium-calcium carbonate as (e) the alkaline filler and thymol blue as the organic pH indicator dye.

Amounts

Preferably, (b) the Bronsted base is present in an amount of 1 to 5000 parts by weight relative to 1 part by weight of (a) the organic pH indicator dye compound. More preferably, (b) the Bronsted base is present in an amount of 1000 to 3000 parts by weight, more preferably 1500 to 2500 parts by weight relative to 1 part by weight of (a) the organic pH indicator dye compound.

Preferably, (c) the binder and (d) the optional rheology additive is present in a total amount of 0.02 to 50 parts by weight relative to 1 part by weight of the Bronsted base. More preferably, (c) the binder and (d) the optional rheology additive is present in a total amount of 0.1 to 10 parts by weight, more preferably 0.5 to 2 parts by weight, relative to 1 part by weight of the Bronsted base.

Preferably, (d) the optional rheology additive is present in an amount of 0 to 0.3 parts by weight relative to 1 part by weight of (c) the binder. More preferably, the optional rheology additive is present in an amount of 0.01 to 0.25 parts by weight, more preferably 0.1 to 0.2 parts by weight, relative to 1 part by weight of (c) the binder.

Preferably, (e) the optional alkaline filler is present in an amount of 0 to 10 parts by weight relative to 100 parts by weight of the total composition. More preferably, the optional alkaline filler is present in an amount of 0.1 to 8 parts by weight, more preferably 1 to 7 parts by weight, more preferably 2 to 6 parts by weight, relative to 100 parts by weight of the total composition.

Preferably, the composition according to the invention comprises:
(a) 0.01-7.5 wt % of the organic pH indicator dye compound,
(b) 30-60 wt % of the Bronsted base comprising an organosilane,
(c) 30-60 wt % of the moisture-curable binder,
(d) 0-10 wt % of the optional rheology additive and
(e) 0-10 wt %, preferably 0.1-10 wt %, of the optional alkaline filler.

Process

The humidity indicating composition is prepared by mixing components (a), (b), (c) and optionally (d) and/or (e) in amounts as described hereinabove. The sequence of mixing is not particularly restricted.

Humidity Indication Article

The invention further relates to a process for preparing a humidity indication article, comprising applying the humidity indication composition according to the invention onto at least part of a substrate and allowing the composition to cure.

Due to the absence of a solvent, the process does not require a step of evaporating the solvent which requires an elevated temperature. Instead, the composition is cured which may be completed within a relatively short time at room temperature.

The step of applying the composition according to the invention may involve e.g. dripping droplets of the composition, applying the composition using a brush, screen printing the composition or spraying the composition. Preferably, the step of applying the composition involves spraying the humidity indication composition. It was found that the spraying results in a homogeneous application of the composition.

The composition according to the invention may be applied in a single layer or multiple layers. After the application of the composition according to the invention, a further composition can be applied. Such further composition may be the same composition according to the invention except that it does not comprise component a). In case the application of the composition according to the invention is performed multiple times or a further composition is applied, the previous composition should be sufficiently cured to be tack-free.

Preferably, the composition is applied according to a predetermined pattern, such that the user can clearly determine the color change of the organic pH indicator dye compound.

The invention further relates to the article obtained or obtainable by the process according to the invention.

In another aspect, the invention further relates to a humidity indication article comprising a substrate and a coating made by curing the humidity indication composition according to the invention.

Preferably, the substrate is a fabric. The fabric may be made of polymers such as polyester.

Preferably, the substrate is in the form of a container such that it can contain or enclose products. It is herein understood that the term 'container' means any article which has an open space in which products can be contained or enclosed. Examples of the container are bags and boxes.

Preferably, the products contained in the container comprise a desiccant, such as silica gel, aluminum phyllosilicates, bentonite or calcium chloride.

Preferably, the article is a reusable article, meaning the article is suitable for being subjected to a drying process at an elevated temperature, such as by microwave or oven.

In another aspect, the invention relates to an article comprising a substrate and a coating provided on the substrate, wherein the substrate is in the form of an enclosure and the article comprises a desiccant enclosed in the substrate, wherein the coating does not contain heavy metal and wherein the coating has a yellow color at a relative humidity of 0% and a blue color at a relative humidity of 100%. Such article is particularly advantageous in that the color change and therefore change in the humidity level is intuitive.

It is noted that the invention relates to all possible combinations of features described herein, preferred in particular are those combinations of features that are present in the claims. It will therefore be appreciated that all combinations of features relating to the composition according to the invention; all combinations of features relating to the process according to the invention and all combinations of features relating to the composition according to the invention and features relating to the process according to the invention are described herein.

It is further noted that the term 'comprising' does not exclude the presence of other elements. However, it is also to be understood that a description on a product/composition comprising certain components also discloses a product/composition consisting of these components. The product/composition consisting of these components may be advantageous in that it offers a simpler, more economical process for the preparation of the product/composition. Similarly, it is also to be understood that a description on a process comprising certain steps also discloses a process consisting of these steps. The process consisting of these steps may be advantageous in that it offers a simpler, more economical process.

The invention is now elucidated by way of the following examples, without however being limited thereto.

EXPERIMENTS

Example 1

A composition described in Table 1 was applied to a bag made of polyester fabric by spraying. It was possible to obtain a very well defined pattern with a controlled thickness with a thickness of 650-700 μm. The composition was dried to form a coating. Subsequently, the bag with the coating was filled with silica beads and closed. The bag was placed in the humidity chamber (40° C., 75% humidity). Once the silica beads in the bag were full of humidity, the bag was dried in a microwave (700 W, 3×4 minutes). The cycle of placing of the bag in the humidity chamber followed by drying in a microwave was repeated 8 times.

TABLE 1

| all amounts in wt % | |
| --- | --- |
| | Ex 1 |
| 3-aminopropyltriethoxysilane (Dynasylan AMEO) and thymol blue* | 54.6 |
| polyether-based silane-terminated polymer (Geniosil XB502) | 39.5 |
| rheology additive 1 (polyhydroxycarboxylic acid esters) (Byk R606) | 3.1 |
| rheology additive 2 (silica and aluminium oxide) (Aerosil COK84) | 2.8 |

*The amount of thymol blue was 0.05 wt % with respect to the total of 3-aminopropyltriethoxysilane and thymol blue.

The coating was of a dark khaki green color when the coating was formed. As the coating absorbed moisture, the coating turned dark grey blue color. The change of the color was gradual, indicating the amount of the absorbed moisture by the color.

After drying the bag in a microwave, the color of the coating turned back to dark khaki green. A similar color change behavior was observed in each of the 8 cycles. It can therefore be understood that the bag according to the invention can be used as a color indicator many times by drying.

Examples 2-3

Example 1 was repeated using different compositions as shown in Table 2.

TABLE 2

| all amounts in wt % | | |
| --- | --- | --- |
| | Ex 2 | Ex 3 |
| 3-aminopropyltriethoxysilane (Dynasylan AMEO) and thymol blue* | 53.6 | 48.4 |
| polyether-based silane-terminated polymer (Geniosil XB502) | 38.8 | 42.9 |
| rheology additive 1 (polyhydroxycarboxylic acid esters) (Byk R606) | 3.2 | 3.2 |
| rheology additive 2 (silica and aluminium oxide) (Aerosil 200) | 4.4 | 0 |
| partially hydrated magnesium-calcium carbonate (Portafill H5) | 0 | 5.6 |

*The amount of thymol blue was 0.05 wt % with respect to the total of 3-aminopropyltriethoxysilane and thymol blue.

The colors of the compositions were observed at (1) the dry state, (2) after 6.5 h at 40° C., 75% relative humidity, which resulted in 15.9% humidity intake, and (3) after 24 h at 40° C., 75% relative humidity, which resulted in 27.2% humidity intake. The changes in the colors between conditions (1), (2) and (3) were more distinct with the composition of Ex 3 than that of Ex 2.

Comparative Experiment

The performance of a humidity indicating composition (which is similar to CCE 1 of EP2339340) which does not include the components of the present invention was tested.

A drop of a composition described in Table 3 was applied to a bag made of polyester fabric.

TABLE 3

| all amounts in wt % | |
| --- | --- |
| | CEx |
| ethanol | 46.82 |
| water | 25.43 |
| sulfuric acid conc. | 3.12 |
| ascorbic acid | 8.48 |
| neutral red | 0.04 |
| glycerine | 16.11 |

A part of the composition did not stay on the surface of the bag and penetrated through the fabric. Hence the shape of the drop was not well-defined.

The bag was placed in the humidity chamber (40° C., 75% humidity) for 24 hours and the composition absorbed water. Although a color change was noted, the composition further spread out on the surface of the bag and the shape of the coating was not maintained.

Further experiments similar to Example 1 were performed using phenolphthalein, thymolphthalein and thiazol yellow instead of thymol blue in order to confirm that humidity indicating compositions could be obtained with other organic pH indicator dye compounds in the composition according to the invention, and that the obtained compositions could be successfully applied to a polyester substrate. It was confirmed that coatings could be obtained that changed colors by the change in the moisture level and that the coatings could be durably applied to a substrate.

What is claimed is:

1. A humidity indicating composition comprising:
   (a) an organic pH indicator dye compound,
   (b) a Bronsted base comprising an organosilane,
   (c) a moisture-curable binder,
   (d) an optional rheology additive and
   (e) an alkaline filler comprising a carbonate of an alkaline earth metal, and
   wherein the "composition contains less than 0.01 part by weight of solvent relative to 1 part by weight of the composition prior to application to a substrate or cure of the moisture-curable binder.

2. The humidity indicating composition according to claim 1, wherein the organosilane comprises a Bronsted base group selected from the group consisting of NH2, NHR, NR2, amide and pyridine functionalities, wherein R is a C1-C20 alkyl substituent or a C6-C20 aryl substituent.

3. The humidity indicating composition according to claim 1, wherein the organosilane is aminoalkyltrialkoxysilane.

4. The humidity indicating composition according to claim 1, wherein the binder is a polyether-based silane-terminated polymer.

5. The humidity indicating composition according to claim 1, wherein the composition comprises the rheology additive and the rheology additive is selected from the group consisting of polyhydroxycarboxylic acid esters, particles of fumed silica and particles of fumed silica and aluminium oxide.

6. The humidity indicating composition according to claim 1, wherein the organic pH indicator dye compound is selected from alizarin red S, alizarin yellow GG, alizarin yellow R, brilliant yellow, bromocresol green, bromophenol blue, bromothymol blue, chlorophenol red, clayton yellow, congo red, cresol red, crystal violet, dimethyl yellow, erythrosine, malachite green, metacresol purple, metanil yellow, methyl green, methyl orange, methyl red, neutral red, phenolphthalein, phenol red, paramethyl red, quinaldine red, resazurin, thymolphthalein and thymol blue.

7. The humidity indicating composition according to claim 1, wherein the composition comprising the organic pH indicator dye compound undergoes a color transition at a pH range which lies within a pH range of 5-12.

8. The humidity indicating composition according to claim 1, wherein (e) the alkaline filler is present in an amount of 0.1 to 8 parts by weight relative to 100 parts by weight of the total composition.

9. The humidity indicating composition according to claim 1, comprising:
   (a) 0.01-7.5 wt % of the organic pH indicator dye compound,
   (b) 30-60 wt % of the Bronsted base comprising an organosilane,
   (c) 30-60 wt % of the moisture-curable binder,
   (d) 0-10 wt % of the optional rheology additive and
   (e) 0.1-10 wt %, of the alkaline filler.

10. The humidity indicating composition according to claim 1, wherein the total weight of the components (a)-(e) is at least 90 wt % of the total composition.

11. A process for preparing a humidity indication article comprising applying the humidity indication composition according to claim 1 onto at least part of a substrate and allowing the composition to cure.

12. The humidity indication article obtained or obtainable by the process according to claim 11.

13. The article according to claim 12, wherein the substrate is a fabric.

14. The article according to claim 13, wherein the substrate is in the form of an enclosure and the article comprises a desiccant enclosed in the substrate.

15. The article according to claim 12, wherein the substrate is in the form of an enclosure and the article comprises a desiccant enclosed in the substrate.

16. An article comprising a substrate and a coating comprising the composition according to claim 1 provided on the substrate, wherein the substrate is in the form of an enclosure and the article comprises a desiccant enclosed in the substrate, wherein the coating does not contain heavy metal and wherein the coating has a yellow color at a relative humidity of 0% and a blue color at a relative humidity of 100%.

17. The humidity indicating composition according to claim 1, wherein the composition comprising the organic pH indicator dye compound undergoes a color transition at a pH range which lies within a pH range of 7-12, wherein (e) the alkaline filler is present in an amount of 1 to 7 parts by weight, relative to 100 parts by weight of the total composition, and wherein the total weight of the components (a)-(e) is at least 95 wt % of the total composition.

18. The humidity indicating composition according to claim 1, wherein the composition comprising the organic pH indicator dye compound undergoes a color transition at a pH range which lies within a pH range of 7-9.5, wherein (e) the alkaline filler is present in an amount of 2 to 6 parts by weight, relative to 100 parts by weight of the total composition, and wherein the total weight of the components (a)-(e) is at least 98 wt % of the total composition.

* * * * *